United States Patent [19]  
Reusser

[11] Patent Number: 4,542,249  
[45] Date of Patent: Sep. 17, 1985

[54] OLEFIN CONVERSIONS AND CATALYSTS
[75] Inventor: Robert E. Reusser, Bartlesville, Okla.
[73] Assignee: Phillips Petroleum Company, Bartlesville, Okla.
[21] Appl. No.: 607,051
[22] Filed: May 4, 1984
[51] Int. Cl.[4] .............................................. C07C 3/62
[52] U.S. Cl. .................................... 585/329; 585/646; 585/671
[58] Field of Search ................ 585/324, 671, 646, 329
[56] References Cited

U.S. PATENT DOCUMENTS

| | | | |
|---|---|---|---|
| 3,457,320 | 7/1969 | Stapp et al. | 260/683 |
| 3,538,182 | 11/1970 | Kahn et al. | 260/683.2 |
| 3,660,516 | 5/1972 | Crain et al. | 260/683 |
| 3,660,517 | 5/1972 | Reusser et al. | 260/683 |
| 3,729,524 | 4/1973 | Reusser | 260/683 |
| 3,760,026 | 9/1973 | Reusser et al. | 260/683 |
| 3,767,565 | 10/1973 | Banks | 208/93 |
| 3,781,377 | 12/1973 | Myers | 260/683.2 |
| 3,792,106 | 2/1974 | Regier | 260/683 |

*Primary Examiner*—Curtis R. Davis
*Attorney, Agent, or Firm*—Howard D. Doescher

[57] ABSTRACT

The disproportionation/skeletal isomerization of olefins can be carried out with high conversions and selectivity in the presence of catalyst compositions containing Group IIA and at least one of Group VIB and rhenium components.

19 Claims, No Drawings

OLEFIN CONVERSIONS AND CATALYSTS

This invention relates to the conversion of olefins according to the olefin reaction, to catalysts therefor, and to a method for modifying the activity of such catalysts.

BACKGROUND

Certain conversion reactions involving unsaturated reactants are generally of low yield and selectivity to desired products. Certain reactions involving the shifting of double bonds and/or the rearrangement of substituents in the same or different molecules are of low to moderate efficiency—i.e., with conversion rates and selectivities on the order of 50 percent or less.

OBJECTS OF THE INVENTION

It is an object of the invention to provide a catalyst composition useful for the conversion of olefin reactants to desired products.

It is another object to provide a process for the molecular rearrangement or skeletal isomerization of olefins.

It is yet another object to provide a process for the disproportionation of one or more olefinic molecules.

It is still another object of the invention to employ a combination of polymerization(s), skeletal isomerization(s), and disproportion(s) in the production of conversion products from certain olefins.

INVENTION

It has been discovered that in the disproportionation and skeletal isomerization of certain chemical species, good conversion and reaction selectivity can be achieved via the use of a catalyst which contains a Group IIA metal component and at least one of a Group VIB metal and rhenium.

In accordance with one broad embodiment of the invention, the total dimerization effluent is passed directly to disproportionation and the total disproportionation reaction effluent is passed directly to skeletal isomerization.

In accordance with another broad embodiment of the invention, the dimerization catalyst, the disproportionation catalyst, and the skeletal isomerization catalyst are all positioned in series in a common reaction zone without reaction product separation between catalyst zones.

In accordance with a further broad embodiment of the invention, skeletal isomerization of olefins is carried out in the presence of a tungsten oxide-silica olefin reaction catalyst modified by depositing magnesium oxide on the surface thereof.

In another embodiment according to the invention, a process is provided comprising (a) reacting diisobutylene and ethylene under disproportionation conditions to produce neohexene, and (b) subjecting the total disproportionation reaction effluent containing neohexene without separation to skeletal isomerization to form dimethylbutenes.

More specifically, the diisobutylene feed for disproportionation described above in (a) is formed by the dimerization of isobutylene.

In one embodiment, the production of 2,3-dimethylbutenes by the skeletal isomerization of neohexene uses magnesium oxide deposited on $WO_3/SiO_2$ catalysts as an isomerization catalyst. Neohexene conversions of greater than 90 percent with greater than 90 percent selectivity to 2,3-dimethylbutenes are thereby obtained. Contrastingly, a physical mixture of MgO and $WO_3/SiO_2$ gives predominantly di-tertiary-butylethylene from neohexene under similar reaction conditions.

In another embodiment, the production of 2,3-dimethylbutenes directly from isobutylene is accomplished by passing isobutylene plus ethylene over a dimerization catalyst such as nickel oxide on alumina or $H_3PO_4$ on Kieselguhr, then over a disproportionation catalyst such as $WO_3/SiO_2$ and MgO followed by contact with a skeletal isomerization catalyst such as eta-alumina. Good conversions of isobutylene, i.e., greater than 60 percent, and high selectivity to 2,3-dimethylbutene, i.e., greater than 80 percent, are attained with no need to isolate or to purify intermediate neohexene prior to skeletal isomerization to desired 2,3-dimethylbutenes.

In yet another embodiment, 2,3-dimethylbutenes are produced by the skeletal isomerization of neohexene which is prepared by the disproportionation of diisobutylene with ethylene. The process involves feeding the effluent of an isobutylene dimerization reactor directly over a disproportionation catalyst followed by contact with a skeletal isomerization catalyst. Thus, 2,3-dimethylbutenes are obtained from ethylene plus isobutylene feed.

ADVANTAGES

The catalyst and processes of the instant invention have several advantages over the prior art.

The catalyst's ingredients are relatively inexpensive chemicals which, when combined in accordance with the invention, produce olefin conversion catalysts of superior efficiency.

The processes which employ the subject catalysts are economical due to the inexpensive character of the catalyst composition. Furthermore, when properly combined in accordance herewith, compositions containing the subject catalyst assist in the above-mentioned reactions so that high conversion rates and selectivities are commonly attained.

In at least one of its aspects, the invention simplifies the preparation of 2,3-dimethylbutenes by eliminating the need for separate preparations of diisobutylene and neohexene. Thus, the same reactor and/or stacked or sequential catalysts can be employed herein. This results in substantial saving in energy, time, and equipment.

Other objects, aspects, and the several advantages of the invention will become apparent from consideration of the description and appended claims.

DETAILED DESCRIPTION OF THE INVENTION

There are three chemical conversion processes involved in this invention that result in the formation of 2,3-dimethylbutenes from isobutylene and ethylene and there are three catalyst systems used to bring about these conversions. The conversion processes involved are (a) dimerization of isobutylene to diisobutylene, (b) disproportionation of diisobutylene and ethylene to produce neohexene and (c) isomerization of neohexene to 2,3-dimethylbutenes.

The particular catalysts which are employed in the various catalytic reaction zones of this process are not critical to the invention but solid type catalysts are preferred.

A. Catalyst for Dimerization of Isobutylene

The isobutylene dimerization step can employ any suitable catalyst which is capable of dimerizing isobutene. The preferred dimerization catalyst is one which will produce relatively high quantities of diisobutylene (2,4,4-trimethylpentene-1 and 2,4,4-trimethylpentene-2) with relatively small amounts of other $C_8$ isomers or higher isobutene oligomers. Some examples of suitable dimerization catalysts are cold sulfuric acid; phosphoric acid on Kieselguhr; silica/alumina sometimes promoted with Ni, Co, Fe, Pt or Pd; activated natural clays plus activating substances such as ZnO; metallic phosphates such as those of iron (III) and cerium optionally supported on carriers such as activated carbon; bauxite; activated carbon alone and with metal halides such as $TiCl_2$; heteropolyacids such as silicotungstic acid on silica gel and phosphomolybdic acid; $BF_3H_3PO_4$ and $BF_3HPO_3$; dihydroxyfluoroboric acid; HF and fluorides or oxyfluorides of S, Se, N, P, Mo, Te, W, V and Si boiling below 300° C.; $BF_3$-diethyl ether complexes; $BF_3$-hydrocarbon complexes; $BF_3$—$SO_2$; and $AlCl_3$ with cocatalysts such as diethyl ether, HCl, and nitromethane. These catalysts and dimerization processes, including operating conditions, are known in the art. The preferred catalyst for this present application is NiO on alumina or $H_3PO_4$ on Kieselguhr.

B. Catalyst for Disproportionation of Diisobutylene with Ethylene

In the olefin disproportionation step of the invention, the effluent from the dimerization zone is mixed with ethylene and contacted with any suitable olefin disproportionation catalyst. Suitable olefin disproportionation catalysts for use in the process of the present invention are any of the catalysts which have ability for converting propylene to ethylene and butene. These catalysts are sometimes referred to as "olefin reaction" catalysts. These catalysts are now well known in the art. The method of preparation and the use of these olefin disproportionation catalysts are known in the art. Solid olefin disproportionation catalysts are presently preferred. Some examples of the preferred catalyst systems are molybdenum oxide on alumina, tungsten oxide on silica or alumina, and rhenium oxide on alumina.

The olefin disproportionation catalyst is utilized in conjunction with a suitable double bond isomerization catalyst. The presence of the olefin isomerization catalyst, intimately mixed with the olefin disproportionation catalyst, increases the per pass conversion of the diisobutylene to the desired neohexene product and recyclable by-products. Any double bond isomerization catalyst which is compatible with the olefin disproportionation catalyst of choice may be utilized. The presently preferred catalyst combination is a fixed catalyst bed which comprises an intimate mixture of a particulate activated MgO double bond isomerization catalyst and a particulate activated $WO_3/SiO_2$ olefin disproportionation catalyst.

Other suitable catalysts include aluminum phosphate, zirconium phosphate, calcium phosphate, magnesium phosphate or titanium phosphate, promoted by one or more of a sulfide of molybdenum or tungsten, or by an oxide or of a compound convertible to the oxide on calcination, of molybdenum, tungsten, or rhenium, or by magnesium tungstate or beryllium phosphotungstate. These catalysts can be in the form of a powder, or granules, as well as a variety of other shapes as is known in the art.

C. Catalyst for Isomerization of Neohexene to 2,3-dimethylbutenes

The catalyst for the skeletal isomerization of neohexene to 2,3-dimethylbutenes is comprised of a support component and metal component. In one embodiment the catalyst is comprised of a Group IIA component added by precipitation, co-precipitation, sequential precipitation, or impregnation by spraying, etc. onto a support containing at least one component of a Group VI B metal and rhenium.

The Group IIA Components

The Group IIA component comprises at least one alkaline earth metal containing substance. The Group IIA metals contemplated include beryllium, magnesium, calcium, strontium, and barium. Magnesium is preferred. Mixtures of Group IIA element-containing materials can be employed.

The anionic portion of the Group IIA component is not critical. It is preferred that it be hydroxide, oxide or other ion convertible to the oxide upon activation of the Group VIB or rhenium component upon which the Group IIA component is deposited.

The Group VIB or Rhenium Component

The Group VIB and rhenium component contains two subcomponents: one containing a Group VIB or rhenium ingredient; and one containing a support ingredient.

The Group VIB or Rhenium Ingredient

The Group VIB and rhenium substances useful herein include at least one metal selected from rhenium, molybdenum, and tungsten. Tungsten is preferred.

The anionic portion of the Group VIB ingredient is not critical. It is important, however, that it be one which affords compatibility with the support ingredient and the Group IIA component.

The Support Ingredient

The support comprises a solid inorganic refractory oxide containing a major proportion of alumina or silica. Such materials are commonly known as refractory oxides and include, for example, silica, alumina, magnesia-alumina, silica-alumina, titania-alumina, zirconia-alumina, alumina-titania-zirconia, thoria, aluminum phosphate, zirconium phosphate, calcium phosphate, magnesium phosphate, thorium phosphate and titanium phosphate. Preferred refractory metal oxides are silica refractory oxides, i.e., refractory oxides containing a substantial proportion of silica, e.g., at least 90 percent by weight of silica, preferably at least 99 percent of silica although still larger proportions of silica can be used. Generally, the refractory oxide has a surface area of at least 10 m²/g and preferably the surface area is from about 25 m²/g to 800 m²/g.

The tungsten or molybdenum oxide component of the catalyst of the invention for the isomerization of the neohexene can be incorporated onto the silica support by any suitable method including, for example, impregnation, and coprecipitation.

Preferred combinations of the above support materials with the oxides of tungsten and molybdenum promoter materials include (1) silica or thoria promoted by the oxide, or a compound convertible to an oxide by calcination, of tungsten or molybdenum; (2) alumina promoted by an oxide, or compound convertible to an oxide by calcination, of tungsten or molybdenum; and (3) one or more of the group aluminum phosphate, zirconium phosphate, calcium phosphate, magnesium phosphate, thorium phosphate or titanium phosphate promoted by one or more of an oxide of tungsten or molybdenum, or by a compound of tungsten or molybdenum convertible to an oxide by calcination.

The solid component of the catalysts can be in any conventional catalytic shape or size, depending upon the type of conversion in which it is to be utilized. For example, in fixed bed catalyst systems, the solid composite can be in the form of spheres, pellets, extrudates, agglomerates, and the like. In slurry catalyst systems, the solid can be in the form of relatively small particles or in the form of a powder.

To be effective in the present catalyst system for isomerization and disproportionation, the above-described tungsten or molybdenum components of the catalysts is activated at elevated temperatures, generally in flowing air. The activation of the catalysts is accomplished at a temperature of from about 300° C. to about 800° C. (572° F. to 1472° F.) for a period of several minutes to several hours or longer. When the solid component of the catalyst system is tungsten oxide on silica, a convenient and economical treatment is in the temperature range of 400°–700° C. (752° F. to 1292° F.) for 0.5 to 20 hours or longer. In some cases the activation using an oxygen-containing gas can be followed by treatment, also at elevated temperatures, with other treating gases such as carbon monoxide, hydrogen, and the like.

The oxide of molybdenum or tungsten or rhenium is preferably combined with the inorganic oxide solid support in a high positive oxidation state, e.g., hexavalent tungsten or hexavalent molybdenum or hexavalent rhenium. The proportion of the tungsten, rhenium, or molybdenum oxide combined with the inorganic oxide support can be varied, but generally the inorganic oxide solid contains at least 0.1 percent by weight of the oxide of tungsten, rhenium, or molybdenum with amounts from about 0.2 percent to about 30 percent by weight being preferred, although still larger (major) proportions of tungsten, rhenium, or molybdenum oxide can be used. The weight percent referred to is based on the combined weights of the support and the metal.

D. Reactants

The reactants employed in the disproportionation and isomerization processes of the invention are selected with particular conversion products in mind. Generally, they are olefinic feeds or reactants containing from about 1 to about 30 carbon atoms and having at least one site of carbon to carbon unsaturation.

The reactants preferred for the dimerization step of the reaction will be those olefins conforming to the general formula:

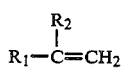
(I)

wherein, $R_1$ and $R_2$ are independently chosen from $C_1$–$C_4$ alkyl moieties. Thus, they will on dimerization over a suitable catalyst, such as $NiO/Al_2O_3$, $H_3PO_4$/Kieselghur, cold $H_2SO_4$, $SiO_2/Al_2O_3$ sometimes promoted with a group VIII metal, or others such as are known in the art, form a neoalkyl substituted olefin. A preferred olefin for this dimerization is isobutylene, which dimerizes to 2,4,4-trimethylpentenes (1- and 2- isomers).

The reactants preferred for the disproportionation step of the reaction are:

(II)

wherein $R_1$–$R_3$ are independently selected from $C_1$–$C_4$ alkyl groups and $R_4$–$R_7$ are independently selected from hydrogen or $C_1$–$C_4$ alkyl groups. The dimer of isobutylene, i.e. the 1- and 2-isomers of 2,4,4-trimethylpentene, is readily available and is the preferred compound for this disproportionation reaction. Disproportionation of this molecule with ethylene produces one molecule of neohexene and one molecule of isobutylene, which can be recycled for dimerization. Ethylene is the preferred co-reactant with compound (II) although other compounds of the general formula

(III)

where $R_8$–$R_{11}$ are independently selected from hydrogen and $C_1$–$C_{10}$ alkyl moieties, can be used.

The reactants preferred for the isomerization (third) step of the reaction are alpha-olefins containing at least one neoalkyl group adjacent to the olefinic carbon conforms to the general formula:

(IV)

wherein $R_1$–$R_3$ are independently selected from $C_1$–$C_4$ alkyl groups. Most preferred is neohexene in which $R_1$–$R_3$ is each a methyl group. Under the conditions of the rearrangement reaction these reactants undergo skeletal isomerization to form

(V)

In one preferred embodiment, an isobutylene dimerization effluent is passed directly to catalytic disproportionation and the disproportionation effluent is then passed directly to skeletal isomerization.

EXAMPLE I

Dimerization of Isobutylene

Isobutylene was dimerized by passing through a bed of 0.5 g NiO on alumina (catalyst A) mixed with 10 grams of low surface area (1.5 m²/g) alumina at 66°–93° C. (150°–200° F.) and 400 psig with 150 WHSV. The catalyst bed had been heated under air at 538° C. (1000 F.) for 2.5 hours and cooled down under nitrogen prior to use. A 43.6% conversion of the isobutylene was obtained with 52.5% selectivity to diisobutylene (1- and 2-isomers).

EXAMPLE II

Preparation of WO$_3$/SiO$_2$ Catalyst

Catalyst B: A tungsten oxide catalyst was prepared with a WO$_3$ content of 6 weight percent based on the total weight of tungsten oxide and silica. The catalyst was prepared by impregnating high surface area silica with ammonium metatungstate [(NH$_4$)$_2$W$_4$O$_{13}$.8H$_2$O]. The impregnation was accomplished by treating the silica with an aqueous solution of the ammonium metatungstate. The impregnated silica was dried and calcined in air at 500° C. (932° F.) to convert the metatungstate to the oxide. A $-20+60$ mesh sieve fraction was obtained for use as described below.

EXAMPLE III

MgO Precipitated on WO$_3$/SiO$_2$

Catalyst C: Twenty five grams of the WO$_3$/SiO$_2$ (catalyst B) was added to a solution of 15 grams of MgCl$_2$.6H$_2$O in 100 mL of water, shaken for 10 minutes, and the aqueous solution was decanted from the solid catalyst. Fifty milliliters of concentrated ammonium hydroxide was added to the wet catalyst. After standing for 10 minutes the excess ammonium hydroxide was decanted off and the remaining catalyst was calcined in air at 1000° F. for 3 hours. Carbon monoxide to prereduce the catalyst was passed over the catalyst at 538° C. (1000° F.) for 15 minutes.

EXAMPLE IV

WO$_3$/SiO$_2$ Plus KOH

Catalyst D: onto a WO$_3$/SiO$_2$ (catalyst B in Example II) a solution of KOH was sprayed to leave deposited after drying a 0.1% concentration of KOH. This catalyst was activated in air at 538° (1000° F.) for 2 hours, then 1 part was mixed with 3 parts of MgO and the mixture was again activated in air at 538° C. (1000° F.) for 2.5 hours.

EXAMPLE V

WO$_3$/SiO$_2$ mixed with MgO

Catalyst E: MgO is intimately mixed with WO$_3$/SiO$_2$ (catalyst B) in a 3:1 to 6:1 ratio. The major reaction produced with this catalyt is disproportionation in contrast to catalyst C (example III) which leads mainly to skeletal rearrangement, as demonstrated in U.S. Pat. No. 3,729,524.

EXAMPLE VI

Pure grade isobutylene was passed through a bed of a mixture of equal parts of 13X mole sieve, alumina and magnesium oxide at room temperature. It was then passed through a reactor at 315° C. (600° F.), 400 psig and at 20 WHSV over a catalyst comprised of a mixture of 2.5 grams of WO$_3$/SiO$_2$/0.2% KOH and 8.0 grams of MgO which had been prepared in a manner comparable to that of catalyst D. Approximately 27% conversion of isobutylene was obtained and the product mixture contained 44.0% 2,3-dimethylbutene-2, 24.3% 2,3-dimethylbutene-1 and 5.1% neohexene. This shows that this catalyst results in a conversion of the isobutylene to the desired dimethylbutenes.

EXAMPLE VII

Isobutylene was first percolated over a mixture of silica gel-mole sieve-magnesia at room temperature and then passed through a catalyst bed at 17.2 WHSV, at 371° C. (700° F.), and at 100 psig. The catalyst bed was comprised of WO$_3$/SiO$_2$ (about 8 weight percent WO$_3$) mixed at 1:3.3 ratio with magnesium oxide. A 34.4% conversion of isobutylene with a selectivity to 38.5% 2,3-dimethylbutene-1, 41.1% 2,3-dimethylbutene-2, and 2.5% neohexene.

Under similar conditions except that the WHSV was 19.4 and ethylene was blended with the isobutylene at a 1.73:1 molar ratio, the products contained 20.2% of neohexene, 39.5% of 2,3-dimethylbutene-2 and 21.5% of 2,3-dimethylbutene-1 although only 7.2% conversion was obtained at this higher space velocity.

These runs demonstrate that a mixture of MgO and WO$_3$/SiO$_2$ produces a conversion reaction of isobutylene to 2,3-dimethylbutenes.

EXAMPLE VIII

Isomerization of Neohexene to 2,3-Dimethylbutenes

Neohexene, which had first been percolated through magnesium oxide, was passed over catalyst C (Example III) at 11.6 WHSV at 343° C. (650° F.) and 400 psig. A 92.9% conversion of the neohexene as determined by glc was obtained with 90.5% of the product as 2,3-dimethylbutenes (2:1 ratio of 2-isomer to 1-isomer). This demonstrates the effectiveness of this catalyst in bringing about the isomerization of neohexene to 2,3-dimethylbutenes.

EXAMPLE IX

Disproportionation of Neohexene

When neohexene was treated as in Example VIII except that catalyst E (Example V), i.e. MgO was mixed with the WO$_3$/SiO$_2$ rather than being precipitated on it, a disproportionation of the neohexene to di-t-butylethylene (DTBE) occurred rather than the isomerization to 2,3-dimethylbutenes (DMB). The neohexene was passed over the catalyst at 17.6 WHSV at 343° C. (650° F.) and 100 psig. At 62.8% conversion of the neohexene the selectivity to DTBE was 54.0% and to the DMB was 14.1% as determined by g.l.c. This example, when compared with Example VIII demonstrates the difference in the reaction obtained when the MgO is mixed with the WO$_3$/SiO$_2$ rather than being precipitated on it.

EXAMPLE X

Four grams of WO$_3$/SiO$_2$ containing 0.5% of KOH was mixed with 12.0 grams of MgO containing 1.0% KOH and the mixture was activated for 4 hours at 538° C. (1000° F.) with air passing through the bed. Carbon monoxide was then passed through the bed at 538° C. (1000° C.) for 15 minutes followed by neohexene at 24.7 WHSV, 343° C. (650° F.), and 400 psig pressure. With a 65% conversion of the neohexene, 7% dimethylbutenes and 81% di-t-butylethylene were obtained. Where the magnesium oxide is present in the mixture in a granular form, the predominant reaction is disproportionation rather than skeletal rearrangment.

EXAMPLE XI

2,3-Dimethylbutenes from Diisobutylene and Ethylene

Diisobutylene was purified by passing through a guard bed containing first activated alumina followed by molecular sieve. The diisobutylene was then passed through a catalyst bed comprising 1.8 grams of WO$_3$/SiO$_2$, catalyst B (Example II) and 6.8 grams of MgO followed by a bed of eta alumina with a spacer of quartz chips between the two catalyst components. The reaction was carried out at about 370° C. (700° F.) 300 psig, 25 WHSV with a diisobutylene feed rate of 1.05 mL/minute and an ethylene feed rate of 0.5 mL/minute. Glc analysis of a sample taken after four hours of reaction times showed a diisobutylene conversion of 60.6% with a selectivity to dimethylbutenes of 84.3 wt% (22.9 wt % of the 1-isomer and 61.4% of the 2-isomer). This demonstrates the process of producing dimethylbutenes from diisobutylene and ethylene using a stacked catalyst bed comprised of more than one reaction zone.

EXAMPLE XII 2,3-Dimethylbutenes from Isobutylene and Ethylene

Isobutylene was passed through a mixed bed of $H_3PO_4$ on Kieselguhr (0.5 gram) and alumina (10 grams) at 113 WHSV at 149° C. (300 F.) and 400 psig. The effluent from this reactor was mixed with ethylene at approximately 1:3 ratio and passed through magnesium oxide (4.5 grams) which was mixed with 1.5 grams silica on which was deposited 7.2% $WO_3$ and 0.1% KOH and finally a layer of 5.7 grams of a low sodium zeolite, LZY-82. There was a 68% conversion of the isobutylene and a 19.7% selectivity to 2,3-dimethylbutenes (13.5% 2-isomer and 6.2% 1-isomer). The product mixture also contained 5.0% neohexene and about 70% dimers and trimers of isobutylene. This run demonstrates the process of producing 2,3-dimethylbutenes from isobutylene and ethylene by passing the reactants through separate reaction zones without intermediate product isolation.

I claim:

1. A process for the conversion of alpha-olefins to skeletal isomerization and/or disproportionation products comprising the step of contacting an alpha-olefinic feed with a catalyst composition comprising a Group IIA component deposited onto the surface of a support containing at least one of a Group VI metal and rhenium component.

2. A process according to claim 1 wherein the olefinic feed is suitable for the production of 2,3-dimethylbutenes.

3. A process for the production of 2,3-dimethylbutenes via suitable olefinic conversion comprising the step of contacting an olefin containing at least one neoalkyl group adjacent to an olefinic carbon under conditions to produce 2,3-dimethylbutenes with a catalyst containing MgO deposited by precipitation or impregnation onto the surface of $WO_3/SiO_2$.

4. The process of claim 1 wherein the olefinic feed contains at least one compound conforming to the general formula:

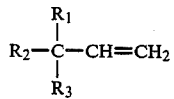

wherein $R_1$-$R_3$ are independently selected from $C_1$-$C_4$ alkyl groups.

5. A process for making skeletal isomerization products from olefins conforming to the formula defined in claim 4 comprising contacting same under isomerization conditions with a catalyst containing Group IIA component deposited by precipitation or impregnation on the surface of a support containing at least one of a Group VIB and rhenium component.

6. A process according to claim 4 wherein the olefinic feed contains neohexene and the product formed contains 2,3-dimethylbutenes.

7. A process for producing disproportionation products from primary reactants and co-reactants comprising the steps of:
   (1) contacting the reactants with a dimerization catalyst,
   (2) contacting the total reaction product of step (1) with a disproportionation catalyst,
   (3) contacting the total disproportionation product of step (2) with an isomerization catalyst under skeletal isomerization conditions, and
   (4) isolating the desired product.

8. The process of claim 7 wherein the primary reactant is at least one compound conforming to the general formula:

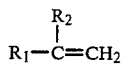

wherein $R_1$-$R_2$ are independently chosen from $C_1$-$C_4$ alkyl moieties.

9. The process of claim 8 wherein the co-reactant is at least one compound conforming to the general formula:

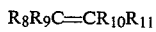

wherein $R_8$-$R_{11}$ are independently selected from hydrogen and $C_1$-$C_{10}$ alkyl groups.

10. The process of claim 9 wherein the primary reactant is isobutylene and the co-reactant is ethylene.

11. The process of claim 10 wherein the dimerization effluent is passed directly to the disproportionation and the disproportionation effluent is passed directly to skeletal isomerization.

12. A process for the production of dimethylbutenes from diisobutylene which comprises
   (a) contacting diisobutylene and ethylene under disproportionation conditions in the presence of disproportionation catalyst to form a product mixture comprising 3,3-dimethylbutene-1(neohexene), 2,3-dimethylbutene-2, and 2,3-dimethylbutene-1 and
   (b) subjecting the product mixture of (a) without isolation of neohexene intermediate to skeletal isomerization conditions in the presence of an isomerization catalyst to convert neohexene to 2,3-dimethylbutene-2 and 2,3-dimethylbutene-1.

13. A process according to claim 12 wherein said isomerization catalyst in (b) is MgO deposited onto the surface of $WO_3/SiO_2$.

14. A process according to claim 12 wherein said disproportionation catalyst in (a) is $WO_3/SiO_2$ mixed with MgO.

15. A process according to claim 12 wherein diisobutylene for step (a) is formed by dimerization of isobutylene and the total dimerization product is mixed with ethylene and passed as feed to disproportionation step (a).

16. A process according to claim 15 wherein dimerization catalyst, disproportionation catalyst and skeletal isomerization catalyst are stacked in series in the same reactor so that dimethylbutenes can be produced from isobutylene by passing the reactants through separate reaction zones without intermediate product isolation.

17. A process for the isomerization of olefins which comprises contacting olefinic hydrocarbons under isomerization conditions with a catalyst comprising $WO_3/SiO_2$ which is modified by depositing MgO on the surface thereof.

18. A process according to claim 17 wherein the olefinic hydrocarbons are neoalkyl substituted olefins.

19. A process according to claim 18 wherein the neoalkyl substituted olefin is neohexene which is converted to 2,3-dimethylbutenes.

* * * * *